US005622854A

United States Patent [19]
Draper

[11] Patent Number: 5,622,854
[45] Date of Patent: Apr. 22, 1997

[54] METHOD AND REAGENT FOR INHIBITING T-CELL LEUKEMIA VIRUS REPLICATION

[75] Inventor: Kenneth G. Draper, Solon, Ohio

[73] Assignee: Ribozyme Pharmaceuticals Inc., Boulder, Colo.

[21] Appl. No.: 192,941

[22] Filed: Feb. 7, 1994

Related U.S. Application Data

[63] Continuation of Ser. No. 882,714, May 14, 1992, abandoned.

[51] Int. Cl.[6] .......................... C12N 15/85; C12Q 1/68; A61K 48/00
[52] U.S. Cl. .................. 435/366; 435/6; 435/91.31; 435/172.3; 435/320.1; 435/325; 536/23.1; 536/23.2; 536/24.5; 514/44
[58] Field of Search .................. 435/6, 91.31, 320.1, 435/172.3, 240.1, 252.3, 240.2; 536/23.2, 23.1, 24.5; 514/44

[56] References Cited

U.S. PATENT DOCUMENTS 5,168,053  12/1992  Altman et al. .......................... 514/44

FOREIGN PATENT DOCUMENTS 9115580  10/1991  WIPO.

OTHER PUBLICATIONS

Rossi et al. J. Cell. Biochem. Suppl. 14A p. 428, 1990.
Sarver et al. Science 247:4947:1222–25, 1990, cited as Biotech Abstr Acc #: 90–05661.
Matsukura et al. PNAS 86:4244, 1989.
Cheng–Mayer et al. Science 246:1629, 1989.
Viscidi et al. Science 246:1606, 1989.
Malim et al. PNAS 86:8222, 1989.
Terwilliger PNAS 88:10971, 1991.
Bartel et al. Cell 67:529, 1991.
Taylor, et al., "Ribozyme–Mediated Cleavage of an HIV–1 gag RNA: The Effects of Nontargeted Sequences and Secondary Structure on Ribozyme Cleavage Activity", 1 *Antisense Res and Dev* 173, 1991.
Sambrook, et al., "Molecular Cloning: A Laboratory Manual", published by Cold Spring Harbor Laboratory Press (N.Y.), pp. 7.71–7.78, 1989.
Usman et al., "Automated Chemical Synthesis of Long Oligoribonucleotides Using 2'–O–Silylated Ribonucleoside 3'–0–Phosphoramidites on a Controlled–Pore Glass Support: Synthesis of a 43–Nucleotide Sequence Similar to the 3'–Half Molecule of an *Escherichia coli* Formylmethionine tRNA", 109 *Jrnl of Amer. Chem. Society*, 7845, 1987.
Slim et al., "Configurationally Defined Phosphorothioate–Containing Oligoribonucleotides in the Study of the Mechanism of Cleavage of Hammerhead Ribozymes", 19 *Nucl Acids Res.* 1183, 1991.
Tsukiyama–Kohara et al., "Internal Ribosome Entry Site Within Hepatitis C Virus RNA", 66 *Jrnl of Virol.* 1476, 1992.

Hampel et al., "RNA Catalyst for Cleaving Specific RNA Sequences", filed Sep. 20, 1989 which is a Continuation–in–Part of U.S. Ser. No. 07/247,100 filed Sep. 20, 1988.
Perrotta and Been, 31 *Biochemistry* 16, 1992.
Hampel and Tritz, 28 *Biochemistry* 4929, 1989.
Hampel et al., 18 *Nucleic Acids Research* 299, 1990.
Weerasinghe et al., 65 *Journal of Virology* 5531, 1991.
Mamone et al., "Design of Hammerhead Ribozymes Targeted to Sequences in HIV, HSV, and the RAT ANF GENE", Abstract of Keystone, CO (May 27, 1992).
Pavco et al., "Regulation of Self–Splicing Reactions by Antisense RNA", Abstract of Keystone, CO (May 27, 1992).
Haseloff and Gerlach, 334 *Nature* 585, 1988.
Guerrier–Takada et al., 35 *Cell* 849, 1983.
Koizumi et al., 117 *Gene* 179, 1992, "Ribozymes Designed to Inhibit Transformation of NIH3T3 Cells by the Activated c–Ha–ras Gene".
Sioud and Drlica, 88 *Proc. Natl. Acad. Sci. USA* 7303, 1991, "Prevention of Human Immunodeficiency Virus Type 1 Integrase Expression in *Escherichia coli* by a Ribozyme".
Sarver et al., 247 *Science* 1222, 1990, "Ribozymes as Potential Anti–HIV–1 Therapeutic Agents".
Scanlon et al., 88 *Proc. Natl. Acad. Sci. USA* 10591, 1991, "Ribozyme–Mediated Cleavage of c–fos mRNA Reduces Gene Expression of DNA Synthesis Enzymes and Metallothionein".
Chuat and Galibert, 162 *Biochemical and Biophysical Research Communications* 1025, 1989, "Can Ribozymes be Used to Regulate Procaryote Gene Expression?".
Dropulic et al., 66 *Journal of Virology* 1432, 1992, "Functional Characterization of a U5 Ribozyme: Intracellular Suppression of Human Immunodeficiency Virus Type I Expression".
Sarver et al., 2 *AIDS Res. Revs.* 259, 1992, "Catalytic RNAs (Ribozymes): A New Frontier in Biomedical Applications".
Kashani–Sabet et al., 2 *Antisense Research & Development* 3, 1992, "Reversal of the Malignant Phenotype by an Anti–ras Ribozyme".
Chen et al., 20 *Nucleic Acids Research* 4581, 1992, "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates".
Cameron and Jennings, 86 *Proc. Natl. Acad. Sci. USA* 9139, 1989, "Specific Gene Suppression by Engineered Ribozymes in Monkey Cells".
Weerasinghe et al., 65 *Journal of Viology* 5531, 1991, "Resistance to Human Immunodeficiency Virus Type 1 (HIV–1) Infection in Human CD4[+] Lymphocyte–Derived Cell Lines Conferred by Using Retroviral Vectors Expressing an HIV–1 RNA–Specific Ribozyme".

*Primary Examiner*—John L. LeGuyader
*Attorney, Agent, or Firm*—Lyon & Lyon

[57] ABSTRACT

An enzymatic RNA molecule which specifically cleaves RNA of HTLV–1.

11 Claims, 1 Drawing Sheet

SEQUENCE LISTING ( 1 ) GENERAL INFORMATION:

( i i i ) NUMBER OF SEQUENCES: 25

( 2 ) INFORMATION FOR SEQ ID NO: 1:

( i ) SEQUENCE CHARACTERISTICS:
        ( A ) LENGTH: 14
        ( B ) TYPE: nucleic acid
        ( C ) STRANDEDNESS: single
        ( D ) TOPOLOGY: linear ( i i ) SEQUENCE DESCRIPTION: SEQ ID NO: 1:

CUACGUGUUU GGAG     14

( 2 ) INFORMATION FOR SEQ ID NO: 2:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 2:

AGAGCAUCAG AUCACC     16

( 2 ) INFORMATION FOR SEQ ID NO: 3:

( i ) SEQUENCE CHARACTERISTICS:
           ( A ) LENGTH: 25
           ( B ) TYPE: nucleic acid
           ( C ) STRANDEDNESS: single
           ( D ) TOPOLOGY: linear ( i i ) SEQUENCE DESCRIPTION: SEQ ID NO: 3:

GGCUCAGCUC UACAGUUCCU AUCCC                                                           25

( 2 ) INFORMATION FOR SEQ ID NO: 4:

( i ) SEQUENCE CHARACTERISTICS:
           ( A ) LENGTH: 27
           ( B ) TYPE: nucleic acid
           ( C ) STRANDEDNESS: single
           ( D ) TOPOLOGY: linear ( i i ) SEQUENCE DESCRIPTION: SEQ ID NO: 4:

CCCCUCCUUC CCCACCCAGA GAACCUC                                                   27

( 2 ) INFORMATION FOR SEQ ID NO: 5:

( i ) SEQUENCE CHARACTERISTICS:
           ( A ) LENGTH: 25
           ( B ) TYPE: nucleic acid
           ( C ) STRANDEDNESS: single
           ( D ) TOPOLOGY: linear ( i i ) SEQUENCE DESCRIPTION: SEQ ID NO: 5:

CCCCGCCAAU CACUCAUACA ACCCC                                                           25

( 2 ) INFORMATION FOR SEQ ID NO: 6:

( i ) SEQUENCE CHARACTERISTICS:
           ( A ) LENGTH: 25
           ( B ) TYPE: nucleic acid
           ( C ) STRANDEDNESS: single
           ( D ) TOPOLOGY: linear ( i i ) SEQUENCE DESCRIPTION: SEQ ID NO: 6:

CAACAUUCCA CCCUCCUUCC UCCAG                                                           25

( 2 ) INFORMATION FOR SEQ ID NO: 7:

( i ) SEQUENCE CHARACTERISTICS:
           ( A ) LENGTH: 21
           ( B ) TYPE: nucleic acid
           ( C ) STRANDEDNESS: single
           ( D ) TOPOLOGY: linear ( i i ) SEQUENCE DESCRIPTION: SEQ ID NO: 7:

GGCCAUGCGC AAAUACUCCC C                                                                    21

( 2 ) INFORMATION FOR SEQ ID NO: 8:

( i ) SEQUENCE CHARACTERISTICS:
           ( A ) LENGTH: 16
           ( B ) TYPE: nucleic acid
           ( C ) STRANDEDNESS: single
           ( D ) TOPOLOGY: linear ( i i ) SEQUENCE DESCRIPTION: SEQ ID NO: 8:

CGAAAUGGAU ACAUGG                                                                           16

( 2 ) INFORMATION FOR SEQ ID NO: 9:

( i ) SEQUENCE CHARACTERISTICS:
    ( A ) LENGTH: 14
    ( B ) TYPE: nucleic acid
    ( C ) STRANDEDNESS: single
    ( D ) TOPOLOGY: linear ( i i ) SEQUENCE DESCRIPTION: SEQ ID NO: 9:

CCUGUCUUUU CCAG     14

( 2 ) INFORMATION FOR SEQ ID NO: 10:

( i ) SEQUENCE CHARACTERISTICS:
    ( A ) LENGTH: 16
    ( B ) TYPE: nucleic acid
    ( C ) STRANDEDNESS: single
    ( D ) TOPOLOGY: linear ( i i ) SEQUENCE DESCRIPTION: SEQ ID NO: 10:

CAAAACCUGU ACACCC     16

( 2 ) INFORMATION FOR SEQ ID NO: 11:

( i ) SEQUENCE CHARACTERISTICS:
    ( A ) LENGTH: 24
    ( B ) TYPE: nucleic acid
    ( C ) STRANDEDNESS: single
    ( D ) TOPOLOGY: linear ( i i ) SEQUENCE DESCRIPTION: SEQ ID NO: 11:

CAUGUACCUC UACCAGCUUU CCCC     24

( 2 ) INFORMATION FOR SEQ ID NO: 12:

( i ) SEQUENCE CHARACTERISTICS:
    ( A ) LENGTH: 13
    ( B ) TYPE: nucleic acid
    ( C ) STRANDEDNESS: single
    ( D ) TOPOLOGY: linear ( i i ) SEQUENCE DESCRIPTION: SEQ ID NO: 12:

CCCCCAUCAC CUG     13

( 2 ) INFORMATION FOR SEQ ID NO: 13:

( i ) SEQUENCE CHARACTERISTICS:
    ( A ) LENGTH: 15
    ( B ) TYPE: nucleic acid
    ( C ) STRANDEDNESS: single
    ( D ) TOPOLOGY: linear ( i i ) SEQUENCE DESCRIPTION: SEQ ID NO: 13:

AGAUUGGUAG UAANA     15

( 2 ) INFORMATION FOR SEQ ID NO: 14:

( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i i ) SEQUENCE DESCRIPTION: SEQ ID NO: 14:

GCCCUAAUAA UUCUACCC     18

( 2 ) INFORMATION FOR SEQ ID NO: 15:

( i ) SEQUENCE CHARACTERISTICS:
    ( A ) LENGTH: 23

( B ) TYPE: nucleic acid
        ( C ) STRANDEDNESS: single
        ( D ) TOPOLOGY: linear ( i i ) SEQUENCE DESCRIPTION: SEQ ID NO: 15:

CACCCGUCAC GCUGACAGCC UGG 23

( 2 ) INFORMATION FOR SEQ ID NO: 16:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 16:

CCACUCAACC CUCACC 16

( 2 ) INFORMATION FOR SEQ ID NO: 17:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 17:

ACCGAUGGCA CGCCUAUGAU UUCCG 25

( 2 ) INFORMATION FOR SEQ ID NO: 18:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear ( i i ) SEQUENCE DESCRIPTION: SEQ ID NO: 18:

CUACAGUCCU CCUCCUUUAU AUUUC 25

( 2 ) INFORMATION FOR SEQ ID NO: 19:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) SEQUENCE DESCRIPTION: SEQ ID NO: 19:

CUACCACCCC UCAUUUCUAC UCUCAC 26

( 2 ) INFORMATION FOR SEQ ID NO: 20:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 20:

CGGCCUCAUA CAGUACUCUU CC 22

( 2 ) INFORMATION FOR SEQ ID NO: 21:

( i ) SEQUENCE CHARACTERISTICS:
        ( A ) LENGTH: 14
        ( B ) TYPE: nucleic acid
        ( C ) STRANDEDNESS: single (D) TOPOLOGY: linear (ii) SEQUENCE DESCRIPTION: SEQ ID NO: 21:

CCUUUCAUAA UUUG 14

(2) INFORMATION FOR SEQ ID NO: 22:

(i) SEQUENCE CHARACTERISTICS:
      (A) LENGTH: 23
      (B) TYPE: nucleic acid
      (C) STRANDEDNESS: single
      (D) TOPOLOGY: linear (ii) SEQUENCE DESCRIPTION: SEQ ID NO: 22:

AUUUGAAGAA UACACCAACA UCC 23

(2) INFORMATION FOR SEQ ID NO: 23:

(i) SEQUENCE CHARACTERISTICS:
      (A) LENGTH: 19
      (B) TYPE: nucleic acid
      (C) STRANDEDNESS: single
      (D) TOPOLOGY: linear (ii) SEQUENCE DESCRIPTION: SEQ ID NO: 23:

AUUUCUCUAC UUUUUAACG 19

(2) INFORMATION FOR SEQ ID NO: 24:

(i) SEQUENCE CHARACTERISTICS:
      (A) LENGTH: 11
      (B) TYPE: nucleic acid
      (C) STRANDEDNESS: single
      (D) TOPOLOGY: linear (ii) SEQUENCE DESCRIPTION: SEQ ID NO: 24:

CAAAUAUCCC C 11

(2) INFORMATION FOR SEQ ID NO: 25:

(i) SEQUENCE CHARACTERISTICS:
      (A) LENGTH: 14
      (B) TYPE: nucleic acid
      (C) STRANDEDNESS: single
      (D) TOPOLOGY: linear (ii) SEQUENCE DESCRIPTION: SEQ ID NO: 25:

GAGCCUCUCA GUGA 14

METHOD AND REAGENT FOR INHIBITING T-CELL LEUKEMIA VIRUS REPLICATION

This application is a continuation of application Ser. No. 07/882,714, filed May 14, 1992, now abandoned.

BACKGROUND OF THE INVENTION

This invention relates to reagents useful as inhibitors of T-cell leukemia virus (TLV) replication, and in particular, as inhibitors of human T-cell leukemia viruses 1 and 2 (HTLV-I and HTLV-II) replication.

Adult T-cell leukemia (ATL) was first described by workers in Japan. Takatsuki et al., 9 *Jpn. J. Clin. Oncol.* 312, 1979. Since then, the disease has been found in other areas of the Orient, the Caribbean basin, South America and central Africa. The epidemiology has shown a clear association with the presence of a retrovirus known as human T-cell leukemia virus type I (HTLV-I). HTLV-I infection of lymphocytes in vitro results in immortalization of the same cell type as tumor cells, and HTLV-I has proven to be oncogenic in animal model systems, e.g., the rabbit.

HTLV-I was first identified in the HUT 102 cell line (Gallo et al., 43 *Cancer Res.* 3892, 1983), which was established from a patient diagnosed with cutaneous T-cell lymphoma. Yoshida et al., 79 *Proc. Nat. Acad. Sci. USA* 2031, 1982, demonstrated that another cell line, known as MT-1, derived from a patient with ATL, also harbored a C-type retrovirus which was later named HTLV-I.

Since the initial description of ATL and discovery of HTLV-I, the virus has been shown to be associated with other human diseases. The most notable of these is a neurologic disorder known as tropical spastic parapesis (TSP), or HTLV-I associated myelopathy (HAM).

HTLV-II was first described in a T-cell line derived from a patient diagnosed with hairy-cell leukemia. The cell line (Mo-T) was derived from splenic tissue and later shown to harbor a virus which was related to (but distinct from) HTLV-I, and subsequently named HTLV-II. Like HTLV-I, HTLV-II will immortalize lymphocytes. However, limited numbers of HTLV-II associations with disease has precluded epidemiologic demonstration of an etiologic role of the virus in human malignancy.

HTLV is a member of the class of retroviruses that includes bovine leukemia virus (BLV) and simian T-cell leukemia virus (STLV-I). The viruses are grouped within the oncovirus subfamily and are distinct from the other human pathogenic retroviruses, e.g., human immunodeficiency virus (HIV), which belong to the subfamily of lentiviruses. Although the leukemia viruses are oncogenic, they do not harbor oncogenic sequences derived from cellular genomes and their replication is regulated by at least three other genes, known as tax, rex, and pro.

Three mRNA species have been identified for HTLV. The full length RNA, transcribed from the U3-R junction in the 5'LTR and terminating in the R-U5 region of the 3'LTR, is used for the synthesis of gag and pol gene products, and serves as the genomic RNA packaged into virions. A subgenomic RNA with one intron removed serves as the template for env protein synthesis, and a second subgenomic RNA with a second intron removed serves to encode the tax and rex products. The tax initiator codon is the same as that of the env protein and is encoded within the second exon. The rex initiator codon is also within the second exon but is located 59 nucleotides 5' to that of the tax and env.

Unlike the protease genes of the other retroviruses, the HTLV protease gene is encoded by a reading frame which spans the 3' part of the gag region and the 5' part of the pol region, but is distinct from both of the other ORFs. In some of the clones of HTLV-I, mutations in the protease region may be responsible for the lack of infectivity of the clones. The protease is responsible for processing mature gag products and autocatalyzed self-cleavage to produce the mature protease molecule.

Two unique genes are found in HTLV (tax and rex) which encode nonvirion proteins translated from a single, sliced mRNA with three exons. Deletion of sequences within these two genes render infectious clones of HTLV-II noninfectious, providing evidence that the expression of these genes is critical for viral replication.

The HTLV-I and HTLV-II tax genes encode proteins of 40 and 37 kd, respectively. The tax proteins are trans-acting transcriptional activators which increase the rate of transcription initiation from the provital 5'LTR promoter. Using cotransfection techniques, it has been shown that the tax protein is capable of trans-activating heterologous promoters, including the promoters for IL-2 and GM-CSF, c-fos and c-sis.

The rex gene of HTLV-I/HTLV-II encodes proteins of 27 and 21 kd for HTLV-I, and 26 and 24 kd for HTLV-II. The relationship between the two protein species is uncertain. Evidence suggests that the smaller rex protein is synthesized from an internal initiation codon within the same open reading frame. Both rex proteins are phosphorylated and localized in the nucleus of infected cells.

Like the product of the tax gene, the rex protein is essential to the replication of HTLV. Unlike the tax protein, the rex product appears to act post-transcriptionally to regulate viral gene expression. For HTLV-I, rex has been shown to increase the ratio of non-spliced RNA to the fully spliced mRNA which encodes tax and rex. In HTLV-II, rex protein increases the overall level of trans-activation in concert with tax protein. Additionally, in HTLV-II rex has a negative regulatory role which decreases viral mRNA levels. The ultimate effect of rex upon HTLV-I and HTLV-II infected cells is to regulate the levels of expression of genes encoding virion components, thereby determining the production of infectious virions.

The HTLV R and U5 regions are unusually long in comparison to other retroviruses. These regions encode the non-translated leader sequences at the 5' ends of all viral ImRNAs, exhibit extensive secondary structure and probably play a role in the control of translation of those mRNAs.

HTLV-I and HTLV-II share about 65% overall sequence homology at the nucleotide level. The homology is lowest in the LTR and non-translated regions and is highest in the tax and rex genes. Among different HTLV-I isolates, there is 96–99% homology in these two regions. Sequence homology is equally high among the HTLV-II isolates.

Direct cell-to-cell contact appears to be required for efficient HTLV infection. In vitro infection is usually accomplished by cocultivation of target cells with X-ray-irradiated or mitomycin C-treated virus producing cells. Infection by HTLV of susceptible cells is inefficient, with a slow course, as compared to other retrovirus infections. Infection of human cord or peripheral blood lymphocytes by HTLV results in virus production, and eventual immortalization of the cells. Only T-cells have been shown to be transformed by HTLV. Viral replication can occur in other cell types under certain circumstances, such as EBV-transformed B-cells. Productive infection has been observed in a few cells of nonlymphoid origin, most notably human endothelial cells and diploid human fibroblasts.

Infection of cells with HTLV in vitro can usually be accomplished only by cocultivation of the cells to be transformed with virus-infected cells. Proliferating transformed cells predominate in the cultures after 4 or more weeks. Transformed lymphocytes are mostly of the $CD4^+$ phenotype which reflects the observation that tumors in ATL patients are almost invariably of $CD4^+$ type. However, occasional $CD8^+$ tumors have been reported and HTLV can transform $CD8^+$ cells in vitro. Cells transformed in vitro transcribe RNA and produce virions, and these cells can be used to transform other cells. The lack of HTLV gene expression in ATL tumor cells suggests that in vitro transformation does not directly parallel the formation of a leukemic clone in vivo. These differences may reflect differences in selection pressure between in vitro and in vivo transformed clones.

Virion preparations from supernatants of HTLV-infected cells are mitogenic for quiescent human T-cells. Activated T-cells are more easily transformed by HTLV than are quiescent cells. This mitogenic activity of HTLV may be an important evolutionary adaptation because 95% of the T-cells in the body are generally in a quiescent state.

The mitogenic activity of virions suggests a mechanism for HTLV transformation whereby continual stimulation of T-cells via a T-cell receptor results in continuous cell proliferation. The corequisite of tax protein expression resembles the situation observed in transformation of primary rodent fibroblasts in vitro, where coexpression of two oncogenes, one acting in the nucleus and the other at the cell membrane, are required to effect transformation of the cell. Thus, unlike with other retroviruses, it appears that T-cell transformation is a normal course of events for infection with HTLV.

Several categories have been described as stages in ATL. These stages include: (i) asymptomatic carriers; (ii) preleukemic state (pre-ATL); (iii) chronic/smoldering ATL; and (iv) acute ATL. In some cases, these stages may be temporally related. The only significant prognostic factor in acute ATL is the presence of ascites, which is associated with shorter-survival. Despite aggressive chemotherapy, the median survival in acute ATL is measured in months.

The form of disease in some ATL patients is that of a T-cell lymphoma rather than a leukemia. The differential diagnosis of ATL includes other T-cell malignancies such as non-Hodgkins lymphoma, mycosis fungoides, Sezary's syndrome and T-cell chronic lymphocytic leukemia (CLL). One malignancy distinct from ATL in which HTLV-I may play a role is B-cell chronic lymphocytic leukemia (B-cell CLL). There is some evidence for functional impairment of the immune response in ATL patients, as well as some HTLV-I carriers. The role of HTLV-II in the few cases of leukemia associated with viral infection is unclear, since insufficient cases are available for study.

ATL is a highly malignant disease where survival of subacute or acute disease is measured in months. Since only about 1% of patients progress from asymptomatic to acute disease, treatment is reserved for more advanced disease. Standard combination therapies which are used for other aggressive lymphomas and leukemias have not worked for ATL. Other agents such as deoxycoformycin, beta interferon, gamma interferon and anti-Tac antiboby have not been of value in treating ATL.

SUMMARY OF THE INVENTION

The invention features novel enzymatic RNA molecules, or ribozymes, and methods for their use for inhibiting T-cell leukemia virus replication, e.g., HTLV-I, HTLV-II and related viruses, including bovine leukemia virus (BLV) and simian T-cell leukemia virus (STLV-I). Such ribozymes can be used in a method for treatment of diseases caused by these related viruses in man and other animals. The invention also features cleavage of the RNA of these viruses by use of ribozymes. In particular, the ribozyme molecules described are targeted to the nef, vif, tat and rev viral genes. These genes are known in the art, see e.g., Matsukura et al., 86 Proc. Natl. Acad. Sci. USA 4244, 1989, Cheng-Mayer et al., 246 Science 1629, 1989, Viscidi et al., 246 Science 1606, 1989, Malim et al., 86 Proc. Natl. Acad. Sci. USA 8222, 1989, Terwilliger et al., 88 Proc. Natl. Acad. Sci. USA 10971, 1991, and Bartel et al., 67 Cell 529, 1991.

Ribozymes are RNA molecules having an enzymatic activity which is able to repeatedly cleave other separate RNA molecules in a nucleotide base sequence specific manner. Such enzymatic RNA molecules can be targeted to virtually any RNA transcript and efficient cleavage has been achieved in vitro. Kim et al., 84 Proc. Nat. Acad. of Sci. USA 8788, 1987, Hazeloff and Gerlach, 334 234 Nature 585, 1988, Cech, 260 JAMA 3030, 1988, and Jefferies et al., 17 Nucleic Acid Research 1371, 1989.

Ribozymes act by first binding to a target RNA. Such binding occurs through the target RNA binding portion of a ribozyme which is held in close proximity to an enzymatic portion of the RNA which acts to cleave the target RNA. Thus, the ribozyme first recognizes and then binds a target RNA through complementary base-pairing, and once bound to the correct site, acts enzymatically to cut the target RNA. Strategic cleavage of such a target RNA will destroy its ability to direct synthesis of an encoded protein. After a ribozyme has bound and cleaved its RNA target it is released from that RNA to search for another target and can repeatedly bind and cleave new targets.

The enzymatic nature of a ribozyme is advantageous over other technologies, such as antisense technology (where a nucleic acid molecule simply binds to a nucleic acid target to block its translation) since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

Thus, in the first aspect the invention features an enzymatic RNA molecule (or ribozyme) which cleaves T-cell leukemia virus RNA, e.g., HTLV-I RNA, or those other viruses noted above, or their equivalent, in regions required for viral replication, e.g., protein synthesis, e.g., the tax, rex, or pro gene regions, or at structures known to regulate viral gene expression, e.g. the 5'-LTR or 3'-LTR regions.

By "enzymatic RNA molecule" it is meant an RNA molecule which has complementarity in a substrate binding region to a specified gene target, and also has an enzymatic activity which is active to specifically cleave RNA in that target. That is, the enzymatic RNA molecule is able to intermolecularly cleave RNA and thereby inactivate a target RNA molecule. This complementarity functions to allow sufficient hybridization of the enzymatic RNA molecule to the target RNA to allow the cleavage to occur. One hundred percent complementarity is preferred, but complementarity as low as 50–75% may also be useful in this invention. By "equivalent" RNA to HTLV-I is meant to include these naturally occurring RNA molecules associated with leukemic diseases in various animals, including human, feline, and simian. These viral RNAs have similar structures and equivalent genes to each other, including the tax, rex and pro genes.

By "gene" is meant to refer to either the protein coding regions of the cognate mRNA, HTLV genome, proviral genome or any regulatory regions in the RNA which regulate synthesis of the protein or stability of the mRNA.

In preferred embodiments, the enzymatic RNA molecule is formed in a hammerhead motif, but may also be formed in the motif of a hairpin, hepatitis delta virus, group I intron or RNaseP-like RNA (in association with an RNA guide sequence). Examples of such hammerhead motifs are described by Rossi et al. (see citations above), of hairpin motifs by Hampel et al. (see citations above), and an example of the hepatitis delta virus motif is described by Perrotta and Been, 31 *Biochemistry* 16, 1992, of the RNaseP motif by Guerrier-Takada, et al., 35 *Cell* 849, 1983, and of the group I intron by Cech et al., U.S. Pat. No. 4,987,071. These specific motifs are not limiting in the invention and those skilled in the art will recognize that all that is important in an enzymatic RNA molecule of this invention is that it has a specific substrate binding site which is complementary to one or more of the target gene RNA regions, and that it have nucleotide sequences within or surrounding that substrate binding site which impart an RNA cleaving activity to the molecule.

In particularly preferred embodiments, the RNA which is cleaved in HTLV-I RNA or its equivalent is selected from one or more of the following sequences, whose nucleotide numbers are derived from the proviral sequence of the HTLV-I clone HS-35:

| nucleotide number | | |
|---|---|---|
| 7350 | CUACGUGUUUGGAG | (Seq. ID. No. 1) |
| 7448 | AGAGCAUCAGAUCACC | (Seq. ID. No. 2) |
| 7492 | GGCUCAGCUCUACAGUUCCUAUCCC | (Seq. ID. No. 3) |
| 7524 | CCCCUCCUUCCCCACCCAGAGAACCUC | (Seq. ID. No. 4) |
| 7571 | CCCCGCCAAUCACUCAUACAACCCC | (Seq. ID. No. 5) |
| 7596 | CAACAUUCCACCCUCCUUCCUCCAG | (Seq. ID. No. 6) |
| 7620 | GGCCAUGCGCAAAUACUCCCC | (Seq. ID. No. 7) |
| 7645 | CGAAAUGGAUACAUGG | (Seq. ID. No. 8) |
| 7689 | CCUGUCUUUUCCAG | (Seq. ID. No. 9) |
| 7720 | CAAAACCUGUACACCC | (Seq. ID. No. 10) |
| 7758 | CAUGUACCUCUACCAGCUUUCCCC | (Seq. ID. No. 11) |
| 7781 | CCCCCAUCACCUG | (Seq. ID. No. 12) |
| 7804 | CCCCAUGUGAUUUUUUGCCACCCC | (Seq. ID. No. 13) |
| 7909 | GCCCUAAUAAUUCUACCC | (Seq. ID. No. 14) |
| 7967 | CACCCGUCACGCUGACAGCCUGG | (Seq. ID. No. 15) |
| 8010 | CCACUCAACCCUCACC | (Seq. ID. No. 16) |
| 8050 | ACCGAUGGCACGCCUAUGAUUUCCG | (Seq. ID. No. 17) |
| 8110 | CUACAGUCCUCCUCCUUUAUAUUUC | (Seq. ID. No. 18) |

| | | |
|---|---|---|
| 8154 | CUACCACCCCUCAUUUCUACUCUCAC | (Seq. ID. No. 19) |
| 8181 | CGGCCUCAUACAGUACUCUUCC | (Seq. ID. No. 20) |
| 8201 | CCUUUCAUAAUUUG | (Seq. ID. No. 21) |
| 8223 | AUUUGAAGAAUACACCAACAUCC | (Seq. ID. No. 22) |
| 8248 | AUUUCUCUACUUUUUAACG | (Seq. ID. No. 23) |
| 8299 | CAAAUAUCCCC | (Seq. ID. No. 24) |
| 8320 | GAGCCUCUCAGUGA | (Seq. ID. No. 25) |

Other targets include the 5'-LTR region, the protease gene region and the other genes noted above.

In a second related aspect, the invention features a mammalian cell which includes an enzymatic RNA molecule as described above. Preferably, the mammalian cell is a human cell.

In a third related aspect, the invention features an expression vector which includes nucleic acid encoding the enzymatic RNA molecules described above, located in the vector, e.g., in a manner which allows expression of that enzymatic RNA molecule within a mammalian cell.

In a fourth related aspect, the invention features a method for treatment of human leukemic disease by administering to a patient an enzymatic RNA molecule which cleaves HTLV-I RNA or related RNA in the tax, rex, or pro gene regions.

In other related aspects, the invention features treatment of cattle or simians with ribozymes of this invention. Such ribozymes may be identical to those able to cleave HTLV-I or II RNA, or may be modified to target analogous locations in BLV and STLV virus RNAs.

The invention provides a class of chemical cleaving agents which exhibit a high degree of specificity for the viral RNA of HTLV-I or II-infected cells. If desired, such ribozymes can be designed to target equivalent single-stranded DNAs by methods known in the art. The ribozyme molecule is preferably targeted to a highly conserved sequence region of HTLV-I or II such that all strains of HTLV-I or II can be treated with a single ribozyme. Such enzymatic RNA molecules can be delivered exogenously or endogenously to infected cells. In the preferred hammerhead motif the small size (less than 40 nucleotides, preferably between 32 and 36 nucleotides in length) of the molecule allows the cost of treatment to be reduced.

The smallest ribozyme delivered for treatment of HIV infection reported to date (by Rossi et al., 1992 supra) is an in vitro transcript having a length of 142 nucleotides. Synthesis of ribozymes greater than 100 nucleotides in length is very difficult using automated methods, and the therapeutic cost of such molecules is prohibitive. Delivery of ribozymes by expression vectors is primarily feasible using only ex vivo treatments. This limits the utility of this approach. In this invention, an alternative approach uses smaller ribozyme motifs (e.g., of the hammerhead structure, shown generally in FIG. 1) and exogenous delivery. The simple structure of these molecules also increases the ability of the ribozyme to invade targeted regions of the mRNA structure. Thus, unlike the situation when the hammerhead structure is included within longer transcripts, there are no non-ribozyme flanking sequences to interfere with correct folding of the ribozyme structure, as well as complementary binding of the ribozyme to the mRNA target region.

The enzymatic RNA molecules of this invention can be used to treat human leukemia virus infections, including those caused by both HTLV-I and HTLV-II as discussed above. Such treatment can also be extended to other related viruses which infect nonhuman primates including the simian and bovine leukemia viruses. Infected animals can be treated at the time of productive infection. This timing of treatment will reduce viral loads in infected cells and disable viral replication in any subsequent rounds of infection. This is possible because the ribozymes disable those structures required for successful initiation of viral protein synthesis.

The targets chosen in the present invention provide a distinct advantage over prior targets since they do not act only at the time of viral absorption or reverse transcription during infection. In addition, viral particles which are released during a first round of infection in the presence of such ribozymes will still be immunogenic by virtue of having their capsids intact. Thus, one method of this invention allows the creation of defective but immunogenic viral particles, and thus a continued possibility of initiation of an immune response in a treated animal.

In addition, the enzymatic RNA molecules of this invention can be used in vitro in a cell culture infected with HTLV-I, or related viruses, to produce viral particles which have intact capsids and defective genomic RNA. These particles can then be used for instigation of immune responses in a prophylactic manner, or as a treatment of infected animals.

The invention also features immunization preparations formed from defective HTLV-I particles or related particles created by a method of this invention, and methods for immunization or vaccination, e.g., with DNA or vectors encoding a ribozyme of this invention under the control of a suitable promoter.

Other features and advantages of the invention will be apparent from the following description of the preferred embodiments thereof, and from the claims.

DESCRIPTION OF THE PREFERRED EMBODIMENTS

Figure 1:
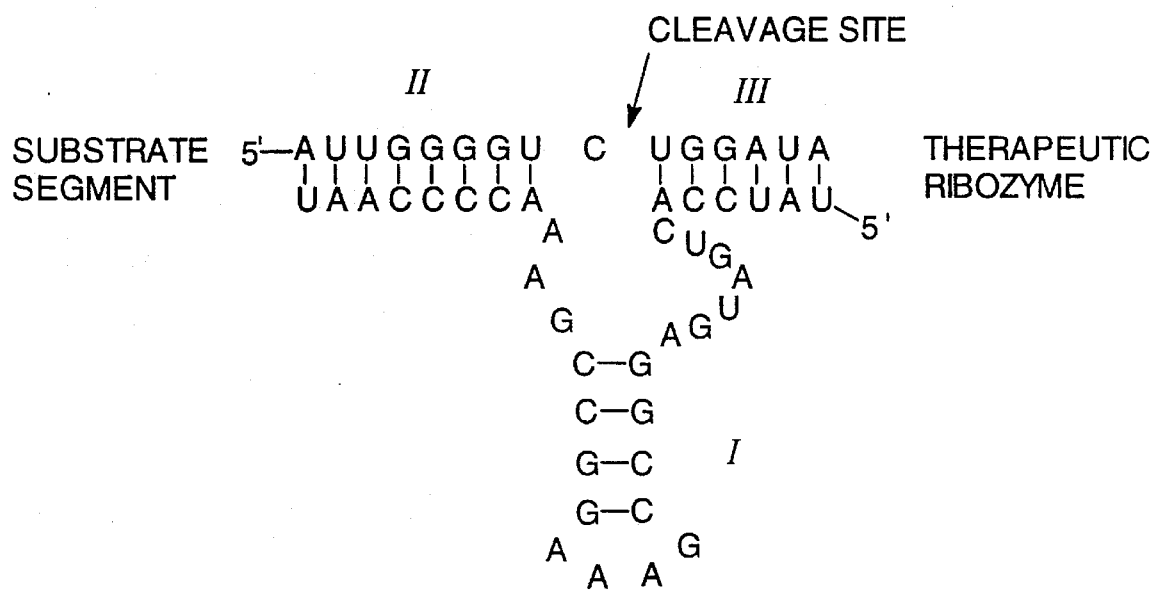

The drawing will first briefly be described.

Drawing

FIG. 1 is a diagrammatic representation of a hammerhead motif ribozyme showing stems I, II and III (marked (I), (II)

and (III) respectively) interacting with a target region. The 5' and 3' ends of both ribozyme and target are shown. Dashes indicate base-paired nucleotides;

Target Sites

The genome of HTLV-I is subject to genetic drift by virtue of its RNA content and the nature of errors in reverse transcription. Those regions (genes) of the genome which are essential for virus replication, however, are expected to maintain a constant sequence (i.e., are conserved) over extensive periods of time. These regions are preferred target sites in this invention since they are more likely to be conserved between different types or strains of immunodeficiency viruses, and thus only one ribozyme is needed to destroy all such viruses. Thus, one ribozyme may be used to target all HTLV-I viruses, as well as all HTLV-II, BLV and STLV viruses. We have selected two genes of HTLV-I which are known to be highly conserved, and examined their nucleotide sequences for the presence of regions which may be cleaved by ribozymes targeted to those regions. Two genes analyzed in detail are the tax and rex genes; the pro gene, the 5'-LTR and other genes noted above can be analyzed in a manner similar to that described below.

Ribozymes targeting selected regions of the HTLV-I genome are chosen to cleave the target RNA in a manner which inhibits translation of the RNA. Genes are selected such that inhibition of translation will inhibit viral replication, e.g., by inhibiting protein synthesis. Selection of effective target sites within these critical regions of HTLV-I RNA entails testing the accessibility of the target RNA to hybridization with various oligonucleotide probes. These studies can be performed using RNA probes and assaying accessibility by cleaving the hybrid molecule with RNaseH (see below). Alternatively, such a study can use ribozyme probes designed from secondary structure predictions of the RNAs, and assaying cleavage products by polyacrylamide gel electrophoresis (PAGE), to detect the presence of cleaved and uncleaved molecules.

The following is but one example of a method by which suitable target sites can be identified and is not limiting in this invention. Generally, the method involves identifying potential cleavage sites for a hammerhead ribozyme, and then testing each of these sites to determine their suitability as targets by ensuring that secondary structure formation is minimal.

The HTLV-I mRNA sequence of the HS-35 clone was analyzed in the regions encoding the tax and rex proteins. Twenty-three putative ribozyme cleavage sites were found to be present in open (weakly base-paired) regions of the mRNA. These represent the preferable sites for hammerhead ribozyme cleavage within these two target RNAs.

Short RNA substrates corresponding to each of the tax and rex gene sites were designed. Each substrate was composed of two to three nucleotides at the 5' and 3' ends that would not base pair with a corresponding ribozyme recognition region. The unpaired regions flanked a central region of 12–14 nucleotides to which complementary arms in the ribozyme were designed.

The structure of each substrate sequence was predicted using a PC fold computer program. Sequences which gave a positive free energy of binding were accepted. Sequences which gave a negative free energy were modified by trimming one or two bases from each of the ends. If the modified sequences were still predicted to have a strong secondary structure, they were rejected.

After substrates were chosen, ribozymes were designed to each of the RNA substrates. Ribozyme folding was also analyzed using PC fold.

Ribozyme molecules were sought which formed hammerhead motif stem II (see FIG. 1) regions and contained flanking arms which were devoid of intramolecular base pairing. Often the ribozymes were modified by trimming a base from the ends of the ribozyme, or by introducing additional base pairs in stem II to achieve the desired fold. Ribozymes with incorrect folding were rejected. After substrate/ribozyme pairs were found to contain correct intramolecular structures, the molecules were folded together to predict intermolecular interactions. A schematic representation of a ribozyme with its coordinate base pairing to its cognate target sequence is shown in FIG. 1.

Using such analyses, the following predictions of effective target sites in the tax and rex genes of the HTLV-I genome, based upon computer generated sequence comparisons, were obtained (see Table 1). The target sequence is listed first with the 5'-most nucleotide number, for reference.

TABLE 1

| Base number | RNA Target sequence | |
|---|---|---|
| 7350 | CUACGUGUUUGGAG | (Seq. ID. No. 1) |
| 7448 | AGAGCAUCAGAUCACC | (Seq. ID. No. 2) |
| 7492 | GGCUCAGCUCUACAGUUCCUAUCCC | (Seq. ID. No. 3) |
| 7524 | CCCCUCCUUCCCCACCCAGAGAACCUC | (Seq. ID. No. 4) |
| 7571 | CCCCGCCAAUCACUCAUACAACCCC | (Seq. ID. No. 5) |
| 7596 | CAACAUUCCACCCUCCUUCCUCCAG | (Seq. ID. No. 6) |
| 7620 | GGCCAUGCGCAAAUACUCCCC | (Seq. ID. No. 7) |

TABLE 1-continued

| Base number | RNA Target sequence | |
|---|---|---|
| 7645 | CGAAAUGGAUACAUGG | (Seq. ID. No. 8) |
| 7689 | CCUGUCUUUUCCAG | (Seq. ID. No. 9) |
| 7720 | CAAAACCUGUACACCC | (Seq. ID. No. 10) |
| 7758 | CAUGUACCUCUACCAGCUUUCCCC | (Seq. ID. No. 11) |
| 7781 | CCCCCAUCACCUG | (Seq. ID. No. 12) |
| 7804 | CCCCAUGUGAUUUUUUGCCACCCC | (Seq. ID. No. 13) |
| 7909 | GCCCUAAUAAUUCUACCC | (Seq. ID. No. 14) |
| 7967 | CACCCGUCACGCUGACAGCCUGG | (Seq. ID. No. 15) |
| 8010 | CCACUCAACCCUCACC | (Seq. ID. No. 16) |
| 8050 | ACCGAUGGCACGCCUAUGAUUCCG | (Seq. ID. No. 17) |
| 8110 | CUACAGUCCUCCUCCUUUAUAUUUC | (Seq. ID. No. 18) |
| 8154 | CUACCACCCCUCAUUUCUACUCUCAC | (Seq. ID. No. 19) |
| 8181 | CGGCCUCAUACAGUACUCUUCC | (Seq. ID. No. 20) |
| 8201 | CCUUUCAUAAUUUG | (Seq. ID. No. 21) |
| 8223 | AUUUGAAGAAUACACCAACAUCC | (Seq. ID. No. 22) |
| 8248 | AUUUCUCUACUUUUUAACG | (Seq. ID. No. 23) |
| 8299 | CAAAUAUCCCC | (Seq. ID. No. 24) |
| 8320 | GAGCCUCUCAGUGA | (Seq. ID. No. 25) |

Those targets thought to be useful as ribozyme targets can be tested to determine accessibility to nucleic acid probes in a ribonuclease H assay (see below). This assay provides a quick test of the use of the target site without requiring synthesis of a ribozyme. It can be used to screen for sites most suited for ribozyme attack.

Synthesis of Ribozymes

Ribozymes useful in this invention can be produced by gene transcription as described by Cech, supra, or by chemical synthesis. Chemical synthesis of RNA is similar to that for DNA synthesis. The additional 2'-OH group in RNA, however, requires a different protecting group strategy to deal with selective 3'–5' internucleotide bond formation, and with RNA susceptibility to degradation in the presence of bases. The recently developed method of RNA synthesis utilizing the t-butyldimethylsilyl group for the protection of the 2' hydroxyl is the most reliable method for synthesis of ribozymes. The method reproducibly yields RNA with the correct 3'–5' internucleotide linkages, with average coupling yields in excess of 99%, and requires only a two-step deprotection of the polymer.

A method, based upon H-phosphonate chemistry gives a relatively lower coupling efficiency than a method based upon phosphoroamidite chemistry. This is a problem for synthesis of DNA as well. A promising approach to scale-up of automatic oligonucleotide synthesis has been described recently for the H-phosphonates. A combination of a proper coupling time and additional capping of "failure" sequences gave high yields in the synthesis of oligodeoxynucleotides in scales in the range of 14 μmoles with as little as 2 equivalents of a monomer in the coupling step. Another alternative approach is to use soluble polymeric supports (e.g., polyethylene glycols), instead of the conventional solid supports. This method can yield short oligonucleotides in hundred milligram quantities per batch utilizing about 3 equivalents of a monomer in a coupling step.

Various modifications to ribozyme structure can be made to enhance the utility of ribozymes. Such modifications will enhance shelf-life, half-life in vitro, stability, and ease of introduction of such ribozymes to the target site, e.g., to enhance penetration of cellular membranes, and confer the ability to recognize and bind to targeted cells.

Exogenous delivery of ribozymes benefits from chemical modification of the backbone, e.g., by the overall negative charge of the ribozyme molecule being reduced to facilitate diffusion across the cell membrane. The present strategies for reducing the oligonucleotide charge include: modification of internucleotide linkages by methylphosphonates, use of phosphoramidites, linking oligonucleotides to positively charged molecules, and creating complex packages composed of oligonucleotides, lipids and specific receptors or effectors for targeted cells. Examples of such modifications include sulfur-containing ribozymes containing phosphorothioates and phosphorodithioates as internucleotide linkages in RNA. Synthesis of such sulfur-modified ribozymes is achieved by use of the sulfur-transfer reagent, $^3$H-1,2-benzenedithiol-3-one 1,1-dioxide. Ribozymes may also contain ribose modified ribonucleotides. Pyrimidine analogues are prepared from uridine using a procedure employing diethylamino sulphur trifluoride (DAST) as a starting reagent. Ribozymes can also be either electrostatically or covalently attached to polymeric cations for the purpose of reducing charge. The polymer can be attached to the ribozyme by simply converting the 3'-end to a ribonucleoside dialdehyde which is obtained by a periodate cleavage of the terminal 2',3'-cis diol system. Depending on the specific requirements for delivery systems, other possible modifications may include different linker arms containing carboxyl, amino or thiol functionalities. Yet further examples include use of methylphosphonates and 2'-o-methylribose and 5' or 3' capping or blocking with $m_7GpppG$ or $m_3^{2,2,7}GpppG$.

For example, a kinased ribozyme is contacted with guanosine triphosphate and guanyltransferase to add a $m^3G$ cap to the ribozyme. After such synthesis, the ribozyme can be gel purified using standard procedure. To ensure that the ribozyme has the desired activity, it may be tested with and without the 5' cap using standard procedures to assay both its enzymatic activity and its stability.

Synthetic ribozymes, including those containing various modifiers, can be purified by high pressure liquid chromatography (HPLC). Other liquid chromatography techniques, employing reverse phase columns and anion exchangers on silica and polymeric supports may also be used.

There follows an example of the synthesis of one ribozyme. A solid phase phosphoramidite chemistry is employed. Monomers used are 2'-tert-butyl-dimethylsilyl cyanoethylphosphoramidities of uridine, N-benzoyl-cytosine, N-phenoxyacetyl adenosine and guanosine (Glen Research, Sterling, Va.). Solid phase synthesis is carried out on either an ABI 394 or 380B DNA/RNA synthesizer using the standard protocol provided with each machine. The only exception is that the coupling step is increased from 10 to 12 minutes. The phosphoramidite concentration is 0.1M. Synthesis is done on a 1 μmole scale using a 1 μmole RNA reaction column (Glen Research). The average coupling efficiencies are between 97% and 98% for the 394 model, and between 97% and 99% for the 380B model, as determined by a calorimetric measurement of the released trityl cation.

Blocked ribozymes are cleaved from the solid support (e.g., CPG), and the bases and diphosphoester moiety deprotected in a sterile vial by dry ethanolic ammonia (2 mL) at 55° C. for 16 hours. The reaction mixture is cooled on dry ice. Later, the cold liquid is transferred into a sterile screw cap vial and lyophilized.

To remove the 2'-tert-butyl-dimethylsilyl groups from the ribozyme, the residue is suspended in 1M tetra-n-butylammonium fluoride in dry THF (TBAF), using a 20 fold excess of the reagent for every silyl group, for 16 hours at ambient temperature (about 15°–25° C.). The reaction is quenched by adding an equal volume of sterile 1M triethylamine acetate, pH 6.5. The sample is cooled and concentrated on a SpeedVac to half the initial volume.

The ribozymes are purified in two steps by HPLC on a C4 300 Å 5 mm DeltaPak column in an acetonitrile gradient.

The first step, or "trityl on" step, is a separation of 5'-DMT-protected ribozyme(s) from failure sequences lacking a 5'-DMT group. Solvents used for this step are: A (0.1M triethylammonium acetate, pH 6.8) and B (acetonitrile). The elution profile is: 20% B for 10 minutes, followed by a linear gradient of 20% B to 50% B over 50 minutes, 50% B for 10 minutes, a linear gradient of 50% B to 100% B over 10 minutes, and a linear gradient of 100% B to 0% B over 10 minutes.

The second step is a purification of a completely deblocked ribozyme by a treatment of 2% trifluoroacetic acid on a C4 300 Å 5 mm DeltaPak column in an acetonitrile gradient. Solvents used for this second step are: A (0.1M Triethylammonium acetate, pH 6.8) and B (80% acetonitrile, 0.1M triethylammonium acetate, pH 6.8). The elution profile is: 5% B for 5 minutes, a linear gradient of 5% B to 15% B over 60 minutes, 15% B for 10 minutes, and a linear gradient of 15% B to 0% B over 10 minutes.

The fraction containing ribozyme is cooled and lyophilized on a SpeedVac. Solid residue is dissolved in a minimum amount of ethanol and sodium perchlorate in acetone. The ribozyme is collected by centrifugation, washed three times with acetone, and lyophilized.

Expression Vector

While synthetic ribozymes are preferred in this invention, those produced by expression vectors can also be used. In designing a suitable ribozyme expression vector the following factors are important to consider. The final ribozyme must be kept as small as possible to minimize unwanted secondary structure within the ribozyme. A promoter (e.g., the HCMV ie1 promoter) should be chosen to be a relatively strong promoter, and expressible both in vitro and in vivo. Such a promoter should express the ribozyme at a level suitable to effect production of enough ribozyme to destroy a target RNA, but not at too high a level to prevent other cellular activities from occurring (unless cell death itself is desired).

A hairpin at the 5' end of the ribozyme is useful to ensure that the required transcription initiation sequence (GG or GGG or GGGAG) does not bind to some other part of the ribozyme and thus affect regulation of the transcription process. The 5' hairpin is also useful to protect the ribozyme from 5'-3' exonucleases. A selected hairpin at the 3' end of the ribozyme gene is useful since it acts as a transcription termination signal, and protects the ribozyme from 3'-5' exonuclease activity. One example of a known termination signal is that present on the T7 RNA polymerase system. This signal is about 30 nucleotides in length. Other 3' hairpins of shorter length can be used to provide good termination and RNA stability. Such hairpins can be inserted within the vector sequences to allow standard ribozymes to be placed in an appropriate orientation and expressed with such sequences attached.

Poly(A) tails are also useful to protect the 3' end of the ribozyme. These can be provided by either including a poly(A) signal site in the expression vector (to signal a cell to add the poly(A) tail in vivo), or by introducing a poly(A) sequence directly into the expression vector. In the first approach the signal must be located to prevent unwanted secondary structure formation with other parts of the ribozyme. In the second approach, the poly(A) stretch may reduce in size over time when expressed in vivo, and thus the vector may need to be checked over time. Care must be taken in addition of a poly(A) tail which binds poly(A) binding proteins which prevent the ribozyme from acting.

Ribozyme Testing

Once the desired ribozymes are selected, synthesized and purified, they are tested in kinetic and other experiments to determine their utility. An example of such a procedure is provided below.

Preparation of Ribozyme

Crude synthetic ribozyme (typically 350 μg at a time) is purified by separation on a 15% denaturing polyacrylamide gel (0.75 mm thick, 40 cm long) and visualized by UV shadowing. Once excised, gel slices containing full length ribozyme are soaked in 5 ml gel elution buffer (0.5M $NH_4OAc$, 1 mM EDTA) overnight with shaking at 4° C. The eluent is desalted over a C-18 matrix (Sep-Pak cartridges, Millipore, Milford, Mass.) and vacuum dried. The dried RNA is resuspended in 50–100 μl TE (TRIS 10 mM, EDTA 1 mM, pH 7.2). An aliquot of this solution is diluted 100 fold into 1 ml TE, half of which is used to spectrophotometrically quantitate the ribozyme solution. The concentration of this dilute stock is typically 150–800 nM. Purity of the ribozyme is confirmed by the presence of a single band on a denaturing polyacrylamide gel.

A ribozyme may advantageously be synthesized in two or more portions. Each portion of a ribozyme will generally have only limited or no enzymatic activity, and the activity will increase substantially (by at least 5–10 fold) when all portions are ligated (or otherwise juxtaposed) together. A specific example of hammerhead ribozyme synthesis is provided below.

The method involves synthesis of two (or more) shorter "half" ribozymes and ligation of them together using T4 RNA ligase. For example, to make a 34 mer ribozyme, two 17 mers are synthesized, one is phosphorylated, and both are gel purified. These purified 17 mers are then annealed to a DNA splint strand complementary to the two 17 mers. This DNA splint has a sequence designed to locate the two 17 mer portions with one end of each adjacent each other. The juxtaposed RNA molecules are then treated with T4 RNA ligase in the presence of ATP. Alternatively, the DNA splint strand may be omitted from the ligation reaction if the complementary binding affects favorable ligation of the two RNA molecules. The 34 mer RNA so formed is then HPLC purified.

Preparation of Substrates

Approximately 10–30 pmoles of unpurified substrate is radioactively 5' end-labelled with T4 polynucleotide kinase using 25 pmoles of [γ-$^{32}$P] ATP. The entire labelling mix is separated on a 20% denaturing polyacrylamide gel and visualized by autoradiography. The full length band is excised and soaked overnight at 4° C. in 100 μl of TE (10 mM Tris-HCl pH 7.6, 0.1 mM EDTA).

Kinetics Reactions

For reactions using short substrates (between 8 and 16 bases) a substrate solution is made 1X in assay buffer (75 mM Tris-HCl, pH 7.6; 0.1 mM EDTA, 10 mM $MgCl_2$) such that the concentration of substrate is less than 1 nM. A ribozyme solution (typically 20 nM) is made 1X in assay buffer and four dilutions are made using 1X assay buffer. Fifteen μl of each ribozyme dilution (i.e., 20, 16, 12, 8 and 4 nM) is placed in a separate tube. These tubes and the substrate tube are pre-incubated at 37° C. for at least five minutes.

The reaction is started by mixing 15 μl of substrate into each ribozyme tube by rapid pipetting (note that final ribozyme concentrations are 10, 8, 6, 4, 2 nM). Five μl aliquots are removed at 15 or 30 second intervals and quenched with 5 μl stop solution (95% formamide, 20 mM EDTA xylene cyanol, and bromphenol blue dyes). Following the final ribozyme time point, an aliquot of the remaining substrate is removed as a zero ribozyme control.

The samples are separated on either 15% or 20% polyacrylamide gels. Each gel is visualized and quantitated with an Ambis beta scanner (Ambis Systems, San Diego, Calif.).

For the most active ribozymes, kinetic analyses are performed in substrate excess to determine $K_m$ and $K_{cat}$ values.

For kinetic reactions with long RNA substrates (greater than 15 bases in length) the substrates are prepared by transcription using T7 RNA polymerase and defined templates containing a T7 promoter, and DNA encoding appropriate nucleotides of the HTLV-I RNA. The substrate solution is made 1X in assay buffer (75 mM Tris-HCl, pH 7.6; 0.1 mM EDTA; 10 mM $MgCl_2$) and contains 58 nanomolar concentration of the long RNA molecules. The reaction is started by addition of gel purified ribozymes to 1 μM concentration. Aliquots are removed at 20, 40, 60, 80 and 100 minutes, then quenched by the addition of 5 μl stop solution. Cleavage products are separated using denaturing PAGE. The bands are visualized and quantitated with an Ambis beta scanner.

Kinetic Analysis

A simple reaction mechanism for ribozyme-mediated cleavage is:

$$R + S \underset{k_{-1}}{\overset{k_1}{\leftrightarrows}} [R:S] \overset{k_2}{\leftrightarrows} [R:P] \boxed{\rightarrow R + P}$$

where R=ribozyme, S=substrate, and P=products. The boxed step is important only in substrate excess. Because ribozyme concentration is in excess over substrate concentration, the concentration of the ribozyme-substrate complex ([R:S]) is constant over time except during the very brief time when the complex is being initially formed, i.e.,:

$$\frac{d[R:S]}{dt} = 0$$

where t=time, and thus:

$$(R)(S)k_1 = (RS)(k_2 + k_1).$$

The rate of the reaction is the rate of disappearance of substrate with time:

$$\text{Rate} = \frac{-d(S)}{dt} = k_2(RS)$$

Substituting these expressions:

$$(R)(S)k_1 = 1/k_2 \frac{-d(S)}{dt}(k_2 + k_1)$$

or:

$$\frac{-d(S)}{S} = \frac{k_1 k_2}{(k_2 + k_1)}(R) dt$$

Integrating this expression with respect to time yields:

$$-\ln \frac{S}{S_0} = \frac{k_1 k_2}{(k_2 + k_1)}(R) t$$

where $S_0$=initial substrate. Therefore, a plot of the negative log of fraction substrate uncut versus time (in minutes) yields a straight line with slope:

$$\text{slope} = \frac{k_1 k_2}{(k_2 + k_1)}(R) = k_{obs}$$

where $k_{obs}$=observed rate constant. A plot of slope ($k_{obs}$) versus ribozyme concentration yields a straight line with a slope which is:

$$\text{slope} = \frac{k_1 k_2}{(k_2 + k_1)} \text{ which is } \frac{k_{cat}}{K_m}$$

Using these equations the data obtained from the kinetic experiments provides the necessary information to determine which ribozyme tested is most useful, or active. Such ribozymes can be selected and tested in in vivo or ex vivo systems.

Liposome Preparation

Lipid molecules are dissolved in a volatile organic solvent ($CHCl_3$, methanol, diethylether, ethanol, etc.). The organic solvent is removed by evaporation. The lipid is hydrated into suspension with 0.1x phosphate buffered saline (PBS), then freeze-thawed 3x using liquid nitrogen and incubation at room temperature. The suspension is extruded sequentially through a 0.4 μm, 0.2 μm and 0.1 μm polycarbonate filters at maximum pressure of 800 psi. The ribozyme is mixed with the extruded liposome suspension and lyophilized to dryness. The lipid/ribozyme powder is rehydrated with water to one-tenth the original volume. The suspension is diluted to the minimum volume required for extrusion (0.4 ml for 1.5 ml barrel and 1.5 ml for 10 ml barrel) with 1xPBS and re-extruded through 0.4 μm, 0.2 μm, 0.1 μm polycarbonate filters. The liposome entrapped ribozyme is separated from untrapped ribozyme by gel filtration chromatography (SEPHAROSE CL-4B, BIOGEL A5M). The liposome extractions are pooled and sterilized by filtration through a 0.2 μm filter. The free ribozyme is pooled and recovered by ethanol precipitation. The liposome concentration is determined by incorporation of a radioactive lipid. The ribozyme concentration is determined by labeling with $^{32}$P. Rossi et al., 1992 supra (and references cited therein) describe other methods suitable for preparation of liposomes.

In Vivo Assay

The efficacy of action of a chosen ribozyme may be tested in vivo by use of cell cultures sensitive to HTLV-I or a related virus, using standard procedures. For example, cultures of HTLV-expressing cells are grown by established procedures. Prior to analysis for ribozyme activity, cultures are treated for 3 to 24 hours with ribozyme-containing liposomes. Cells are then rinsed with phosphate buffered saline (PBS) and viral RNA is harvested for analysis. Alternatively, the cells are treated for three to five days with appropriate liposome preparations. and medium changes. Virus is harvested from both cells and the overlying medium. Cells are broken by three cycles of incubation at −70° C. and 37° C. for 30 minutes at each temperature, and viral titers determined by plaque assay using established procedures.

Ribonuclease Protection Assay

The accumulation of target mRNA in cells or the cleavage of the RNA by ribozymes or RNaseH (in vitro or in vivo) can be quantified using an RNase protection assay.

In this method, antisense riboprobes are transcribed from template DNA using T7 RNA polymerase (U.S. Biochemicals) in 20 μl reactions containing 1X transcription buffer (supplied by the manufacturer), 0.2 mM ATP, GTP and UTP, 1 U/μl pancreatic RNase inhibitor (Boehringer Mannheim Biochemicals) and 200 μCi $^{32}$P-labeled CTP (800 Ci/mmol, New England Nuclear) for 1 h at 37° C. Template DNA is digested with 1 U RNase-free DNase I (U.S. Biochemicals, Cleveland, Ohio) at 37° C. for 15 minutes and unincorporated nucleotides removed by G-50 SEPHADEX spin chromatography.

In a manner similar to the transcription of antisense probe, the target RNA can be transcribed in vitro using a suitable DNA template. The transcript is purified by standard methods and digested with ribozyme at 37° C. according to methods described later.

Alternatively, virus-infected cells are harvested into 1 ml of PBS, transferred to a 1.5 ml EPPENDORF tube, pelleted for 30 seconds at low speed in a microcentrifuge, and lysed in 70 μl of hybridization buffer (4M guanidine isothiocyanate, 0.1% sarcosyl, 25 mM sodium citrate, pH 7.5). Cell lysate (45 μl) or defined amounts of in vitro transcript (also in hybridization buffer) is then combined with 5 μl of hybridization buffer containing $5\times10^5$ cpm of each antisense riboprobe in 0.5 ml Eppendorf tubes, overlaid with 25 μl mineral oil, and hybridization accomplished by heating overnight at 55° C. The hybridization reactions are diluted into 0.5 ml RNase solution (20 U/ml RNase A, 2 U/ml RNase T1, 10 U/ml RNase-free DNAse I in 0.4M NaCl), heated for 30 minutes at 37° C., and 10 μl of 20% SDS and 10 μl of Proteinase K (10 mg/ml) added, followed by an additional 30 minutes incubation at 37° C. Hybrids are partially purified by extraction with 0.5 ml of a 1:1 mixture of phenol/chloroform; aqueous phases are combined with 0.5 ml isopropanol, and RNase-resistant hybrids pelleted for 10 minutes at room temperature (about 20° C.) in a microcentrifuge. Pellets are dissolved in 10 μl loading buffer (95% formamide, 1X TBE, 0.1% bromophenol blue, 0.1% xylene cylanol), heated to 95° C. for five minutes, cooled on ice, and analyzed on 4% polyacrylamide/7M urea gels under denaturing conditions.

Ribozyme Stability

The chosen ribozyme can be tested to determine its stability, and thus its potential utility. Such a test can also be used to determine the effect of various chemical modifications (e.g., addition of a poly(A) tail) on the ribozyme stability and thus aid selection of a more stable ribozyme.

For example, a reaction mixture contains 1 to 5 pmoles of 5' (kinased) and/or 3' labeled ribozyme, 15 μg of cytosolic extract and 2.5 mM $MgCl_2$ in a total volume of 100 μl. The reaction is incubated at 37° C. Eight μl aliquots are taken at timed intervals and mixed with 8 μl of a stop mix (20 mM EDTA, 95% formamide). Samples are separated on a 15% acrylamide sequencing gel, exposed to film, and scanned with an Ambis.

A 3'-labelled ribozyme can be formed by incorporation of the $^{32}$P-labeled cordycepin at the 3' OH using poly(A) polymerase. For example, the poly(A) polymerase reaction contains 40 mM Tris, pH 8, 10 mM $MgCl_2$, 250 mM NaCl, 2.5 mM $MnCl_2$,; 3 μl $P^{32}$ cordycepin, 500 Ci/mM; and 6 units poly(A) polymerase in a total volume of 50 μl. The reaction mixture is incubated for 30 minutes at 37° C.

Effect of Base Substitution Upon Ribozyme Activity

To determine which primary structural characteristics could change ribozyme cleavage of substrate, minor base changes can be made in the substrate cleavage region recognized by a specific ribozyme. For example, the substrate sequences can be changed at the central "C" nucleotide, changing the cleavage site from a GUC to a GUA motif. The $K_{cat}/K_m$ values for cleavage using each substrate are then analyzed to determine if such a change increases ribozyme cleavage rates. Similar experiments can be performed to address the effects of changing bases complementary to the ribozyme binding arms. Changes predicted to maintain strong binding to the complementary substrate are preferred. Minor changes in nucleotide content can alter ribozyme/substrate interactions in ways which are unpredictable based upon binding strength alone. Structures in the catalytic core region of the ribozyme recognize trivial changes in either substrate structure or the three dimensional structure of the ribozyme/substrate complex.

To begin optimizing ribozyme design, the cleavage rates of ribozymes containing varied arm lengths, but targeted to the same length of short RNA substrate can be tested. Minimal arm lengths are required and effective cleavage varies with ribozyme/substrate combinations.

The cleavage activity of selected ribozymes can be assessed using HTLV-I or II-homologous substrates. The assays are performed in ribozyme excess and approximate $K_{cat}/K_{min}$ values obtained. Comparison of values obtained with short and long substrates indicates utility in vivo of a ribozyme.

Intracellular Stability of Liposome-delivered Ribozymes

To test the stability of a chosen ribozyme in vivo the following test is useful. Ribozymes are $^{32}$P-end labeled, entrapped in liposomes and delivered to HTLV-I or II sensitive cells for three hours. The cells are fractionated and ribozyme is purified by phenol/chloroform extraction. Alternatively, cells are collected and washed twice with cold PBS. The cells are homogenized by douncing 35 times in 4 ml of TSE (10 mM Tris, pH 7.4, 0.25M Sucrose, mM EDTA). Nuclei are pelleted at 100xg for 10 minutes. Subcellular organelles (the membrane fraction) are pelleted at 200,000xg for two hours using an SW60 rotor. The pellet is resuspended in 1 ml of H buffer (0.25M Sucrose, 50 mM HEPES, pH 7.4). The supernatant contains the cytoplasmic fraction (in approximately 3.7 ml). The nuclear pellet is resuspended in 1 ml of 65% sucrose in TM (50 mM Tris, pH 74., 2.5 mM $MgCl_2$) and banded on a sucrose step gradient (1 ml nuclei in 65% sucrose TM, 1 ml 60% sucrose TM, 1 ml 55% sucrose TM, 50% sucrose TM, 300 ul 25% sucrose TM) for one hour at 37,000xg with an SW60 rotor. The nuclear band is harvested and diluted to 10% sucrose with TM buffer. Nuclei are pelleted at 37,000xg using an SW60 rotor for 15 minutes and the pellet resuspended in 1 ml of TM buffer. Aliquots are size fractionated on denaturing polyacrylamide gels and the intracellular localization determined. By comparison to the migration rate of newly synthesized ribozyme, the various fraction containing intact ribozyme can be determined.

To investigate modifications which would lengthen the half-life of ribozyme molecules intracellularly, the cells may be fractioned as above and the purity of each fraction assessed by assaying enzyme activity known to exist in that fraction.

The various cell fractions are frozen at −70° C. and used to determine relative nuclease resistances of modified ribozyme molecules. Ribozyme molecules may be synthesized with 5 phosphorothioate (ps), or 2'Omethyl (2'-OMe) modifications at each end of the molecule. These molecules and a phosphodiester version of the ribozyme are end-labeled with $^{32}$P and ATP using T4 polynucleotide kinase. Equal concentrations are added to the cell cytoplasmic extracts and aliquots of each taken at 10 minute intervals. The samples are size fractionated by denaturing PAGE and relative rates of nuclease resistance analyzed by scanning the gel with an Ambis β-scanner. The results show whether the ribozymes are digested by the cytoplasmic extract, and which versions are relatively more nuclease resistant. Modified ribozymes generally maintain 80–90% of the catalytic activity of the native ribozyme when short RNA substrates are employed.

Unlabeled, 5' end-labeled or 3' end-labeled ribozymes can be used in the assays. These experiments can also be performed with human cell extracts to verify the observations.

Administration of Ribozyme

Selected ribozymes can be administered prophylactically, or to HTLV-I infected patients, e.g., by exogenous delivery of the ribozyme to an infected tissue by means of an appropriate delivery vehicle, e.g., a liposome, a controlled release vehicle, by use of iontophoresis, electroporation or ion paired molecules, or covalently attached adducts, and other pharmacologically approved methods of delivery. Routes of administration include intramuscular, aerosol, oral (tablet or pill form), topical, systemic, ocular, intraperitoneal and/or intrathecal. Expression vectors for immunization with ribozymes and/or delivery of ribozymes are also suitable.

The specific delivery route of any selected ribozyme will depend on the use of the ribozyme. Generally, a specific delivery program for each ribozyme will focus on unmodified ribozyme uptake with regard to intracellular localization, followed by demonstration of efficacy. Alternatively, delivery to these same cells in an organ or tissue of an animal can be pursued. Uptake studies will include uptake assays to evaluate cellular ribozyme uptake, regardless of the delivery vehicle or strategy. Such assays will also determine the intracellular localization of the ribozyme following uptake, ultimately establishing the requirements for maintenance of steady-state concentrations within the cellular compartment containing the target sequence (nucleus and/or cytoplasm).

Efficacy and Cytotoxicity can then be tested. Toxicity will not only include cell viability but also cell function.

Some methods of delivery that may be used include:

a. encapsulation in liposomes, b. transduction by retroviral vectors, c. conjugation with cholesterol, d. localization to nuclear compartment utilizing nuclear targeting site found on most nuclear proteins, e. neutralization of charge of ribozyme by using nucleotide derivatives, and f. use of blood stem cells to distribute ribozymes throughout the body.

At least three types of delivery strategies are useful in the present invention, including: ribozyme modifications, particle carrier drug delivery vehicles, and retroviral expression vectors. Unmodified ribozymes, like most small molecules, are taken up by cells, albeit slowly. To enhance cellular uptake, the ribozyme may be modified essentially at random, in ways which reduce its charge but maintains specific functional groups. This results in a molecule which is able to diffuse across the cell membrane, thus removing the permeability barrier.

Modification of ribozymes to reduce charge is just one approach to enhance the cellular uptake of these larger molecules. The random approach, however, is not advisable since ribozymes are structurally and functionally more complex than small drug molecules. The structural requirements necessary to maintain ribozyme catalytic activity are well understood by those in the art. These requirements are taken into consideration when designing modifications to enhance cellular delivery. The modifications are also designed to reduce susceptibility to nuclease degradation. Both of these characteristics should greatly improve the efficacy of the ribozyme. Cellular uptake can be increased by several orders of magnitude without having to alter the phosphodiester linkages necessary for ribozyme cleavage activity.

Chemical modifications of the phosphate backbone will reduce the negative charge allowing free diffusion across the membrane. This principle has been successfully demonstrated for antisense DNA technology. The similarities in chemical composition between DNA and RNA make this a feasible approach. In the body, maintenance of an external concentration will be necessary to drive the diffusion of the modified ribozyme into the cells of the tissue. Administration routes which allow the diseased tissue to be exposed to a transient high concentration of the drug, which is slowly dissipated by systemic adsorption are preferred. Intravenous administration with a drug carrier designed to increase the circulation half-life of the ribozyme can be used. The size and composition of the drug carrier restricts rapid clearance from the blood stream. The carrier, made to accumulate at the site of infection, can protect the ribozyme from degradative processes.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity.

Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver RNA to cells and that the RNA remains biologically active.

For example, a liposome delivery vehicle originally designed as a research tool, Lipofectin, has been shown to deliver intact mRNA molecules to cells yielding production of the corresponding protein. In another study, an antibody targeted liposome delivery system containing an RNA molecule 3,500 nucleotides in length and antisense to a structural protein of HTLV, inhibited virus proliferation in a sequence specific manner. Not only did the antibody target the liposomes to the infected cells, but it also triggered the internalization of the liposomes by the infected cells. Triggering the endocytosis is useful for viral inhibition. Finally, liposome delivered synthetic ribozymes have been shown to concentrate in the nucleus of H9 (an example of an HIV-sensitive cell) cells and are functional as evidenced by their intracellular cleavage of the sequence. Liposome delivery to other cell types using smaller ribozymes (less than 142 nucleotides in length) exhibit different intracellular localizations.

Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nonoparticles and hydrogels may be potential delivery vehicles for a ribozyme. These carriers have been developed for chemotherapeutic agents and protein-based pharmaceuticals, and consequently, can be adapted for ribozyme delivery.

Topical administration of ribozymes is advantageous since it allows localized concentration at the site of administration with minimal systemic adsorption. This simplifies the delivery strategy of the ribozyme to the disease site and reduces the extent of toxicological characterization. Furthermore, the amount of material to be applied is far less than that required for other administration routes. Effective delivery requires the ribozyme to diffuse into the infected cells. Chemical modification of the ribozyme to neutralize negative charge may be all that is required for penetration. However, in the event that charge neutralization is insufficient, the modified ribozyme can be co-formulated with permeability enhancers, such as Azone or oleic acid, in a liposome. The liposomes can either represent a slow release presentation vehicle in which the modified ribozyme and permeability enhancer transfer from the liposome into the infected cell, or the liposome phospholipids can participate directly with the modified ribozyme and permeability enhancer in facilitating cellular delivery. In some cases, both the ribozyme and permeability enhancer can be formulated into a suppository formulation for slow release.

Ribozymes may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the ribozyme to an accessible diseased tissue. Subcutaneous administration drains into a localized lymph node which proceeds through the lymphatic network into the circulation. The rate of entry into the circulation has been shown to be a function of molecular weight or size. The use of a liposome or other drug carrier localizes the ribozyme at the lymph node. The ribozyme can be modified to diffuse into the cell, or the liposome can directly participate in the delivery of either the unmodified or modified ribozyme to the cell. This method is particularly useful for treating T-cell leukemia using anti-HTLV ribozymes of this invention.

Also preferred in T-cell leukemia therapy is the use of a liposome formulation which can deliver ribozymes to lymphocytes and macrophages. This ribozyme delivery system inhibits HTLV proliferation in infected primary immune cells. Whole blood studies show that the formulation is taken up by 90% of the lymphocytes after 8 hours at 37° C. Preliminary biodistribution and pharmacokinetic studies yielded 70% of the injected dose/gm of tissue in the spleen after one hour following intravenous administration. This formulation offers an excellent delivery vehicle for anti-HTLV-I or II ribozymes for two reasons. First, T-helper lymphocytes are the primary cells infected by the virus, and second, a subcutaneous administration delivers the ribozymes to the resident HTLV-infected lymphocytes in the lymph node. The liposomes then exit the lymphatic system, enter the circulation, and accumulate in the spleen, where the ribozyme is delivered to the resident lymphocytes and macrophages.

Intraperitoneal administration also leads to entry into the circulation with the molecular weight or size controlling the rate of entry.

Liposomes injected intravenously show accumulation in the liver, lung and spleen. The composition and size can be adjusted so that this accumulation represents 30% to 40% of the injected dose. The remaining dose circulates in the blood stream for up to 24 hours.

The chosen method of delivery should result in cytoplasmic accumulation and molecules should have some nuclease-resistance for optimal dosing. Nuclear delivery may be used but is less preferable. Most preferred delivery methods include liposomes (10–400 nm), hydrogels, controlled-release polymers, microinjection or electroporation (for ex vivo treatments) and other pharmaceutically applicable vehicles. The dosage will depend upon the disease indication and the route of administration but should be between 100–200 mg/kg of body weight/day. The duration of treatment will extend through the course of the disease symptoms, possibly continuously. The number of doses will depend upon disease delivery vehicle and efficacy data from clinical trials.

Establishment of therapeutic levels of ribozyme within the cell is dependent upon the rate of uptake and degradation. Decreasing the degree of degradation will prolong the intracellular half-life of the ribozyme. Thus, chemically modified ribozymes, e.g., with modification of the phosphate backbone, or capping of the 5' and 3' ends of the ribozyme with nucleotide analogs may require different dosaging. Descriptions of useful systems are provided in the art cited above, all of which is hereby incorporated by reference herein.

The claimed ribozymes are also useful as diagnostic tools to specifically or non-specifically detect the presence of a target RNA in a sample. That is, the target RNA, if present in the sample, will be specifically cleaved by the ribozyme, and thus can be readily and specifically detected as smaller RNA species. The presence of such smaller RNA species is indicative of the presence of the target RNA in the sample.

Other embodiments are within the following claims.

We claim:

1. An enzymatic RNA molecule which specifically cleaves RNA of HTLV-1.

2. The enzymatic RNA molecule of claim 1 which cleaves RNA in the tax, rex, and pro gene regions.

3. The enzymatic RNA molecule of claim 1 which cleaves RNA in the 5'-LTR and 3'-LTR regions.

4. The enzymatic RNA molecule of claim 1 wherein said RNA molecule is in a hammerhead motif.

5. The enzymatic RNA molecule of claim 1 wherein said RNA molecule is in a hairpin, hepatitis Delta virus, group 1 intron, or RNaseP RNA motif.

6. The enzymatic RNA molecule of claim 1 which specifically cleaves a sequence comprising any of SEQ. ID. NOS. 1–25, wherein said enzymatic RNA molecule is in a hammerhead or hepatitis Delta virus motif.

7. The enzymatic RNA of any of claims 1, 2–6 wherein said ribozyme comprises between 5 and 23 bases complementary to the RNA of said gene or region.

8. The enzymatic RNA of any of claim 7 wherein said ribozyme comprises between 10 and 18 bases complementary to the RNA of said gene or region.

9. A mammalian cell including an enzymatic RNA molecule of any of claims 1, 2–6 in vitro.

10. The cell of claim 9, wherein said cell is a human cell.

11. An expression vector including a nucleic acid encoding the enzymatic RNA molecule of any of claims 1, 2–6, in a manner which allows expression of that enzymatic RNA molecule within a mammalian cell, in vitro.

* * * * *